(12) United States Patent
Lee et al.

(10) Patent No.: US 6,228,400 B1
(45) Date of Patent: May 8, 2001

(54) ORALLY ADMINISTERED PHARMACEUTICAL FORMULATIONS OF BENZIMIDAZOLE DERIVATIVES AND THE METHOD OF PREPARING THE SAME

(75) Inventors: Fang-Yu Lee; Shan-chiung Chen; Han-Chiang Kuo, all of Taichung (TW)

(73) Assignee: Carlsbad Technology, Inc., Carlsbad, CA (US)

( * ) Notice: Subject to any disclaimer, the term of this patent is extended or adjusted under 35 U.S.C. 154(b) by 0 days.

(21) Appl. No.: 09/488,406

(22) Filed: Jan. 19, 2000

Related U.S. Application Data
(60) Provisional application No. 60/156,394, filed on Sep. 28, 1999.

(51) Int. Cl.[7] ............................... A61K 9/14; A61K 9/48; A61K 9/16; A01N 43/40
(52) U.S. Cl. ......................... 424/489; 424/451; 424/452; 424/490; 424/493; 424/494; 514/277; 514/336; 514/337; 514/338
(58) Field of Search ................................. 514/277, 336, 514/337, 338; 424/451, 452, 489, 490, 493, 494

(56) References Cited

U.S. PATENT DOCUMENTS

| | | | |
|---|---|---|---|
| 4,255,431 | 3/1981 | Junggren et al. | 424/263 |
| 4,628,098 | 12/1986 | Nohara et al. | 546/271 |
| 4,689,333 | 8/1987 | Nohara et al. | 514/338 |
| 4,738,974 | 4/1988 | Brandstrom | 514/338 |
| 4,786,505 | 11/1988 | Lovgren et al. | 424/468 |
| 5,026,560 | 6/1991 | Makino et al. | 424/494 |
| 5,232,706 | * 8/1993 | Palomo Coll | 424/475 |
| 5,385,739 | 1/1995 | Debregeas et al. | 424/494 |
| 5,948,773 | * 9/1999 | Akiyama et al. | 514/197 |

FOREIGN PATENT DOCUMENTS

| | | |
|---|---|---|
| 124495 | 11/1984 | (EP) . |
| 05194225 | * 8/1993 | (JP) . |
| 07033659 | * 2/1995 | (JP) . |
| WO 9906032 | * 2/1999 | (WO) . |

OTHER PUBLICATIONS

Pilbrant, A. and Cederberg C., Scand. J. Gastroenterol 20(suppl. 108):113–120 (1985).*

* cited by examiner

*Primary Examiner*—Jose' G. Dees
*Assistant Examiner*—Alton Pryor
(74) *Attorney, Agent, or Firm*—Fei-Fei Chao; Venable, Baetjer, Howard & Civiletti, LLP

(57) ABSTRACT

The present invention provides pharmaceutical formulations which contain (a) an inert core of sugar, sugar and starch, or microcrystalline cellulose, (b) a drug emulsion layer which is made from mixing a free base of benzimidazole derivative (such as omeprazole or lansoprazole) with a nonionic surfactant and water, (c) a protective coating which is made of a film-forming compound, and optionally a plasticizer or excipient, and (d) an enteric coating which is made of a pharmaceutically acceptable polymer and a plasticizer. Optionally, a basic amino acid can be added to the drug emulsion layer or the protective coating. The present invention also provides the method for making the pharmaceutical formulations.

23 Claims, No Drawings

US 6,228,400 B1

ORALLY ADMINISTERED PHARMACEUTICAL FORMULATIONS OF BENZIMIDAZOLE DERIVATIVES AND THE METHOD OF PREPARING THE SAME

RELATED APPLICATION

The present invention claims the priority of U.S. Provisional Application Serial No. 60/156,394, filed on Sep. 28, 1999, which is herein incorporated by reference.

FIELD OF THE INVENTION:

This invention relates to novel orally administered pharmaceutical formulations in the form of granules which comprises, as an active ingredient, a potent gastric acid secretion inhibitor, i.e., a substituted 2-(2-benzimidazolyl)-pyridine such as omeprazole or lansoprazole, and the process of making the formulations.

BACKGROUND OF THE INVENTION

Benzimidazole derivatives have been known for their anti-ulcer activities as inhibitors of gastric acid secretion. For example, omeprazole, which has the formula of 5-methoxy-2(((4-methoxy-3,5-dimethyl-2-pyridinyl) methyl)sulfinyl)-1H-benzimidazole), is known for its activity as an inhibitor of $H^+K^+$-ATPase and the proton pump in the gastric mucosa and can be used for the treatment of gastric and duodenal ulcers (Pilbrant and Cederberg, *Scand. J. Gastroenterology* (1985)20:113–120). The information of omeprazole can be found U.S. Pat. No. 4,255,431, U.S. Pat. No. 4,786,505, and EPO 124495. Lansoprazole, which has the formula of 2-[[[3-methyl- 4-(2,2,2-trifluoroethoxy)-2-pyridyl]methyl]sulfinyl]benzimidazole, is useful for prophylaxis and therapy of digestive ulcers (e.g., gastric ulcer, duodenal ulcer) and gastritis. Its empirical formula is $C_{16}H_{14}F_3N_3O_2S$ with a molecular weight of 369.37. The information of lansoprazole can be found U.S. Pat. No. 4,628,098, U.S. Pat. No. 4,689,333, and U.S. Pat. No. 5,026,560.

Omeprazole is very slightly soluble in water, but very soluble in alkaline solutions as the negatively charged ion. It is an ampholyte with $pK_a \sim 4$ (pyridinium) and 8.8 (benzimidazole). Lansoprazole is a white to brownish-white odorless crystalline powder which melts with decomposition at approximately 166° C. Lansoprazole is freely soluble in dimethylformamide; soluble in methanol; sparingly soluble in ethanol; slightly soluble in ethyl acetate, dichloromethane and acetonitrile; very slightly soluble in ether; and practically insoluble in hexane and water.

According to Pilbrant and Cederberg, *Scand. J. Gastroenterology* (1985) 20:113–120, omeprazole is susceptible to degradation/-transformation in acid and neutral media. The rate of degradation proceeds with a half-life of less than 10 minutes at pH-values below 4. At pH 6.5 the half-life of degradation is 18 hours; at pH 11 about 300 days.

Due to the acidic gastric condition, a pharmaceutical dosage form of omeprazole must be coated with an enteric coating to prevent omeprazole from premature contact with gastric juice. However, ordinary enteric coatings are also made of acidic compounds. Therefore, if omeprazole is directly covered with the conventional enteric coating, the dosage form may not only become badly discolored but also decreased in omeprazole content with the passage of time.

To overcome the acidic labile problem and to prolong the storage stability of omeprazole, it is generally recommended to mix omeprazole with an alkaline material so as to create a high pH value for the drug. For instance, U.S. Pat. No. 4,738,974 describes the alkaline salts of omeprazole which include $Li^+$, $Na^+$, $K^+$, $Mg^{2+}$, $Ca^{2+}$, $Ti^{4+}$, $N^+(R^1)_4$ or guanidinium salts.

Alternatively, U.S. Pat. No. 4,786,505 describes an oral dosage form of omeprazole, where omeprazole is mixed with an alkaline reacting substance to create a "micro-pH" around each omeprazole particle of not less than pH=7, preferably not less than pH=8. The alkaline substances described in U.S. Pat. No. 4,786,505 include the sodium, potassium, calcium, magnesium and aluminium salts of phosphoric acid, carbonic acid, citric acid or other suitable weak inorganic or organic acids; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)16CO_3.4H_2O)$, $MgO.Al_2O_3.2SiO_2.nH_2O)$ or similar compounds; organic pH-buffering substances such as trihydroxymethylaminomethane or other similar pH-buffering substances. The high pH-value of omeprazole can be achieved by using an alkaline reacting salt of omeprazole as described in U.S. Pat. No. 4,738,974.

U.S. Pat. No. 5,232,706 describes an oral dosage form of omeprazole which contains a nucleus formed by a mixture of omeprazole or an alkali salt of omeprazole with a first basic compound, a first coating which contains at least an excipient and a second basic compound, and an enteric coating. The basic compounds referred to in U.S. Pat. No. 5,232,706 are sodium, potassium, magnesium, calcium, aluminum or dihydroxyaluminium salts of amino acids, such as glycocoll, glutamic acid, or lysine, or a pyridine carboxylic acids such as nicotinic acid, or organic bases such as guanidine.

Due to the insolubility of omeprazole in water, most of the omeprazole formulations are prepared by mixing the powder form of omeprazole with various kinds of binders, excipients and carriers. For example, U.S. Pat. No. 4,786,505 describes the preparation of the omeprazole core by mixing omeprazole with alkaline reacting substances to form a powder mixture, followed by formulating the powder mixture into small beads, i.e., pellets, tablets, hard gelatine or soft gelatine capsules by conventional pharmaceutical procedures, i.e., by pressing through an extruder and spheronized to pellets.

U.S. Pat. No. 5,385,739 discloses omeprazole microgranules where the powder form of omeprazole is diluted with a substantially equal amount of mannitol powder, together with sodium lauryl sulfate and carboxymethylstarch, so as to produce a homogeneous and stable dilute powder.

U.S. Pat. No. 5,026,560 describes a formulation of making spherical granules containing omeprazole or lansoprazole. The formulation contains a spherical granule which has a core coated with a binder and spraying powder containing the drug and low substituted hydroxypropylcellulose.

In the invention to be described, novel orally administered pharmaceutical formulations of omeprazole or lansoprazole will be described. These formulations are distinctively different from those of the patents described above: First, the invention uses a free base of omeprazole or lansoprazole instead of the alkaline salt form of the drug. Second, the free base of omeprazole or lansoprazole is mixed with a nonionic surfactant and water to form an emulsion, rather than a powder mix, which then can be sprayed and dried onto an inert core to form a granule. Third, the invention demonstrates that it is not necessary to mix the free base of omeprazole or lansoprazole with any alkaline substance in order to create a fully bioavailable dosage form. In fact, the omeprazole formulations in which omeprazole is not mixed with any alkaline substance display equal or better dissolution rate than the commercially available omeprazole formulation such as prilosec where omeprazole is mixed with an alkaline substance.

SUMMARY OF THE INVENTION

A first embodiment of the present invention provides an orally administered pharmaceutical granule of omeprazole or lansoprazole which contains (a) an inert core which is made of starch, a mixture of sugar and starch, or microcrystalline cellulose; (b) a drug emulsion deposited on the inert core, wherein said drug emulsion comprises an effective amount of a free base of omeprazole or lansoprazole, a non-ionic surfactant, a basic amino acid, and water; (c) a protective coating deposited on top of the drug coating, wherein the protective coating comprises at least one film-forming compound which is selected from the group consisting of hydroxypropyl methylcellulose (HPMC), hydroxypropyl cellulose (HPC), polyvinyl pyrrolidone (PVP) and hydroxymethylcellulose (HMC), optionally a plasticizer; and (d) an enteric coating deposited on top of the protective coating, wherein the enteric coating comprises at least a pharmaceutically acceptable polymer which is selected from the group consisting of hydroxypropylmethyl-cellulose phthalate (HPMCP), cellulose acetate phthalate (CAP), co-polymerized methacrylic acid/methacrylic acid methyl esters, and the plasticizer. The pharmaceutical granules can be encapsulated. The granules can also be compressed into tablets by mixing the granule with at least one excipient which is selected from the group consisting of lactose, starch, talc, microcrystalline cellulose, and polyethylene glycol (PEG).

Preferably, the drug emulsion contains 30–60 wt % of water, 1–10 wt % of non-ionic surfactant, and 1–15wt % of basic amino acid. The basic amino acid is used to stabilize the drug and to prevent the drug from decoloration with passage of time. The preferable basic amino acid used for this purpose includes arginine, lysine, histidine, and tryptophane. The most favorable one is arginine. The preferable nonionic surfactant used in the drug emulsion is Poloxamer 188 (polyoxypropylene-polyoxyethylene copolymers having an average molecular weight of 8350) or Tween 80(polysorbates), most favorably Poloxamer 188. The preferable plasticizer used in the protective coating and enteric coating include triethyl citrate, triacetin, and diethyl phthalate, most favorably triethyl citrate. The weight ratio of the polymer and plasticizer in the enteric coating is preferably no less than 10:1, and more preferably no less than 50:1.

The pharmaceutical granule is made by the following steps: (a) preparing an inert core; (b) coating the inert core with a drug emulsion which comprises a free base of omeprazole or lansoprazole, a non-ionic surfactant, a basic amino acid, and water by spraying the drug emulsion onto the inert core which then can be dried using a conventional way, e.g., under warm air; (c) coating the drug emulsion (after drying) with a protective coating which comprises a film-forming compound, a plasticizer, and water by spraying the protective coating onto the dried drug emulsion followed by drying; (d) covering the protective coating with an enteric coating which comprises a polymer, a plasticizer, and water by spraying the enteric coating onto the protective coating.

This pharmaceutical formulation can be used to treat patients with gastrointestinal disorders, including ulcers (e.g., gastric and duodenal ulcers). The treatment includes orally administering a therapeutically effective amount of the formulation to a host in need of such treatment.

The second embodiment of the present invention provides an oral administered pharmaceutical granule of omeprazole or lansoprazole which contains: (a) an inert core which is made of starch, a mixture of sugar and starch, or microcrystalline cellulose; (b) a drug emulsion deposited on the inert core, wherein the drug emulsion comprises an effective amount of a free base of omeprazole or lansoprazole, a non-ionic surfactant, and water, wherein the drug emulsion does not contain an alkaline salt or compound; (c) a protective coating deposited on the drug emulsion, wherein the protective coating comprises at least one film-forming compound which is selected from the group consisting of hydroxypropyl methylcellulose (HPMC), hydroxypropyl cellulose (HPC), polyvinyl pyrrolidone (PVP) and hydroxy methylcellulose, and optionally polyethylene glycol (PEG); and (d) an enteric coating deposited on the protective coating, wherein the enteric coating comprises at least a polymer which is selected from the group consisting of hydroxypropylmethylcellulose phthalate (HPMCP), cellulose acetate phthalate (CAP), and co-polymerized methacrylic acid/methacrylic acid methyl esters, and a plasticizer. The pharmaceutical granules can be encapsulated. The granules can also be compressed into tablets by mixing the granule with at least one excipient which is selected from the group consisting of lactose, starch, talc, microcrystalline cellulose, and polyethylene glycol (PEG).

Preferably, the nonionic surfactant in the drug emulsion is Poloxamer 188 or Tween 80, most favorably Poloxamer 188. Also preferably, the protective coating contains a basic amino acid, e.g., arginine, lysine, histidine, or tryptophane. The most preferable basic amino acid is arginine. The addition of a basic amino acid in the protective coating not only provide better stability for the formulation but also help to prevent the drug from decoloration with the passage of time. PEG is a preferable excipient used in the protective coating. The most preferable PEG is PEG 6000 which has a molecular weight range between 7000 and 9000. The plasticizer used in the enteric coating includes triethyl citrate, triacetin, and diethyl phthalate, preferably triethyl citrate. The weight ratio of the polymer and plasticizer in the enteric coating is preferably no less than 10:1, and more preferably no less than 50:1. In addition, the protective coating can have one or more sublayers. It is preferably that at least one of the sublayers contains a basic amino acid.

The process for making the pharmaceutical granule described in the second embodiment includes the following steps: (a) preparing an inert core; (b) coating the inert core with a drug emulsion which comprises a free base of omeprazole or lansoprazole, a non-ionic surfactant, and water by spraying the drug emulsion onto the inert core, wherein the drug emulsion is free of any alkaline salt or compound; (c) coating the drug emulsion with a protective coating which comprises a film-forming compound, an excipient (e.g., PEG 6000), and water by spraying the protective coating onto the drug emulsion; and (d) covering the protective coating with an enteric coating which comprises a polymer, a plasticizer, and water by spraying said enteric coating onto said protective coating.

The formulation shown in the second embodiment can be used to treat gastro-intestinal disorders, including ulcers (e.g., gastric and duodenal ulcers). The method for treating gastro-intestinal disorders comprise orally administered a therapeutically effective amount of the drug method for treating ulcer comprising orally administering to a host in need of such treatment a therapeutically effective amount of the formulation.

DETAILED DESCRIPTION OF THE INVENTION

The pharmaceutical granule described in the present invention contains four distinctive layers, which are: (1) an inert core, (2) a drug emulsion, (3) a protective coating, and (4) an enteric coating.

The inert core is made of sucrose, starch, talc, or microcrystalline cellulose, alone or in any combination, and is free of any alkaline salt or compound. The inert core can be produced by a granulator by conventional methods or bought from any bulk drug manufacturers. There are three major kinds of inert cores which are commercially available, which are: (1) pure sugar cores; (2) cores containing a mixture of sugar and starch; and (3) microcrystalline cores.

The drug emulsion is produced by mixing the drug, e.g., omeprazole or lansoprazole, with a non-ionic surfactant, e.g., Poloxamer 188 or Tween 80, and water, to form a homogeneous emulsion. Poloxamer 188 is a polyoxypropylene-polyoxyethylene copolymer having an average molecular weight of 8350. Tween 80 is the trademark for polysorbates. Optionally, a basic amino acid, such as arginine, lysine, histidine, and tryptophane, can be added to the drug emulsion. The addition of the basic amino acid in the drug emulsion helps to prevent the drug from decoloration. The drug emulsion has the following advantages over the prior art references disclosed in the "Background of the Invention" section: (1) no binder is needed (in the prior art references, a binder is required because the drug is in the powdery form); (2) no alkaline salt or compound is needed to be mixed with the drug and the drug emulsion helps to preserve the stability and content of the drug with passage of time; and (3) the drug is homogeneously suspended in the emulsion which then can be quantitatively and evenly distributed onto the inert core. The drug emulsion can be coated onto the inert core by conventional coating procedures or sprayed onto the inert core by use of a fluidized bed coating device such as the Glatt or Huttlin machine.

The protective coating serves to separate the drug from the enteric coating. It can contain more than one sublayers. The material for the separating layer is chosen among the pharmaceutically acceptable, water soluble polymers used for film-coating applications, such as hydroxypropylmethyl cellulose (HPMC), hydroxypropyl cellulose (HPC), polyvinyl pyrrolidone (PVP), or hydroxymethyl cellulose (HMC). Optionally, a plasticizer can be added to the protective coating. The plasticizer which can be used in the protective coating includes diethyl phthalate, triacetin, and triethyl citrate. Also optionally, isopropyl alcohol and methylene chloride could be used to replace purified water in the protective coating. In addition, in the protective coating of the second embodiment, optionally an excipient such as PEG 6000 is used to replace the plasticizer. The protective coating can be coated onto the inert core by conventional coating procedures or sprayed onto the inert core by use of a fluidized bed coating device such as the Glatt or Huttlin machine.

The enteric coating serves to protect the drug from contact with acidic gastric juice. The material used in the enteric coating includes Eudragit L, Eudragit S (Rohm Pharma), hydroxypropyl methylcellulose phthalate (HPMCP), or cellulose acetate phthalate (CAP). Eudragit L and Eudragit S are tradenames of co-polymerized methacrylic acid/ methacrylic acid methyl esters. The enteric coating also contain a plasticizer such as diethyl phthalate, triethyl citrate, or triacetin. The weight ratio of the polymer to plasticizer should be no less than 10:1, preferably no less than 50:1. The enteric coating is applied onto the protective layer by conventional coating procedures or sprayed onto the inert core by use of a fluidized bed coating device such as the Glatt or Huttlin machine.

The invention is described in details in the following examples:

EXAMPLE 1

A. Formulation of the Pharmaceutical Granules

| | | |
|---|---|---|
| (1) | Inert Core: 1097.6 g of sugar, sugar plus starch (in any combinations), or microcrystalline cellulose. | |
| (2) | Drug Emulsion: | |
| | Omeprazole | 147 g |
| | Poloxamer 188 | 98 g |
| | Arginine | 78.4 g |
| | Purified Water | 924 ml |
| (3) | Protective Coating: | |
| | HPMC | 78.4 g |
| | Triethyl Citrate | 7.84 g |
| | Purified Water | 784 ml |
| (4) | Enteric Coating Layer: | |
| | Eudragit L30D | 1437.33 g |
| | Triethyl Citrate | 21.56 g |
| | Purified Water | 478.8 ml |

B. Method of Preparing the Formulation

The inert core was either bought from companies selling bulk drug material or prepared using the Glatt machine (a fluidized bed particle making machine imported from Germany).

The drug emulsion was prepared by mixing omeprazole, Poloxamer 188, and arginine in purified water. The emulsion was then placed into the spray gun of the Glatt machine and sprayed onto the core particles while the Glatt machine was set in running (circulating) condition. This would allow the drug to be evenly coated onto the core particles to form drug-coated spherical particles. The drug-coated particles were dried under warm air within the Glatt machine.

Then, a protective coating solution was prepared by mixing HPMC and triethyl citrate in purified water. This coating was then placed into the spray gun of the Glatt machine and sprayed onto the drug-coated particles while the Glatt machine was set in running condition. After the coating was completed, the protective coating-covered particles were again dried under warm air within the Glatt machine.

Finally, an enteric coating was prepared by mixing Eudragit L30D and triethyl citrate in purified water. This coating was placed into the spray gun of the Glatt machine and sprayed onto the protective coating-covered particles to form the pharmaceutical granules before final drying of the granules to complete the process of making the enteric coating-covered granules.

EXAMPLE 2

A. Formulation of Pharmaceutical Granules (1) Inert Core: 1187.41 g of sugar, sugar plus starch (in any combinations), or microcrystalline cellulose.
(2) Drug Emulsion:

| | |
|---|---|
| Lansoprazole | 149.8 (or more) g |
| Poloxamer 188 | 98 g |
| Arginine | 78.4 g |
| Purified Water | 910 ml |

(3) Protective Coating:

| | |
|---|---|
| HPMC | 78.4 g |
| Triethyl Citrate | 7.84 g |
| Purified Water | 784 ml |

(4) Enteric Coating Layer:

| | |
|---|---|
| Eudragit L30D | 1143.3 g |
| Triethyl Citrate | 17.15 g |
| Purified Water | 378 ml |

B. Method of Preparing the Formulation

Same as EXAMPLE 1.

EXAMPLE 3

A. Formulation of Pharmaceutical Granules (1) Inert Core: 1263.15 g of sugar, sugar plus starch (in any combinations), or microcrystalline cellulose.
(2) Drug Emulsion:

| | |
|---|---|
| Omeprazole | 157.5 g |
| Poloxamer 188 | 126 g |
| Arginine | 84 g |
| Purified Water | 855 ml |

(3) Protective Coating:

| | |
|---|---|
| HPMC | 126 g |
| Triethyl Citrate | 12.6 g |
| Isopropyl Alcohol | 1764 ml |
| Methylene Chloride | 756 ml |

(4) Enteric Coating Layer:

| | |
|---|---|
| Eudragit L30D | 1050 g |
| Triethyl Citrate | 15.75 g |
| Purified Water | 345 ml |

B. Method of Preparing the Formulation

Same as EXAMPLE 1.

Tests of the Stability of the Pharmaceutical Formulations as Shown in EXAMPLES 1–3

Table I shows the results of the stability studies of the pharmaceutical formulations as described in EXAMPLES 1–3. The pharmaceutical granules were shelved for 0–6 months at 75% relative humidity and at 30° C., 37° C. and 45° C. A shelf-life of 6 months at 45° C. is equivalent to a shelf-life of 3 years under normal temperature (25° C.).

TABLE 1

STABILITY TEST FOR THE PHARMACEUTICAL GRANULES OF EXAMPLES 1–3

| Temperature (° C.) | Storage Time (Months) | EXAMPLE 1 | EXAMPLE 2 (wt %) | EXAMPLE 3 |
|---|---|---|---|---|
| Control | 0 | 103.5% | 104.1% | 104.5% |
| 30° C. | 1 | 103.3% | 103.1% | 103.9% |
| 30° C. | 2 | 102.7% | 102.7% | 103.1% |
| 30° C. | 3 | 101.4% | 101.9% | 102.5% |
| 30° C. | 6 | 97.3% | 98.0% | 99.7% |
| 37° C. | 1 | 102.1% | 102.7% | 102.3% |
| 37° C. | 2 | 101.1% | 101.3% | 101.5% |
| 37° C. | 3 | 100.1% | 100.9% | 100.1% |
| 37° C. | 6 | 96.5% | 97.2% | 98.7% |
| 45° C. | 1 | 101.1% | 101.0% | 101.6% |
| 45° C. | 2 | 99.7% | 99.3% | 99.2% |
| 45° C. | 3 | 97.3% | 98.2% | 98.7% |
| 45° C. | 6 | 94.8% | 96.4% | 97.4% |

The results of Table I indicate that the pharmaceutical granules of Examples 1–3 possess excellent bioavailability and stability at higher temperatures.

Table II shows the % dissolution, i.e., the percentage of the drug in Examples 1–3 being released in the solution at pH 1.2 (for 120 minutes) and 6.8 (for 30 minutes). The data from the commercially available omeprazole drug (Prilosec®) is included for comparison purpose.

TABLE II

% DISSOLUTION OF THE PHARMACEUTICAL GRANULES OF EXAMPLES 1–3

| | pH 1.2 (120 minutes) | pH 6.8 (30 minutes) |
|---|---|---|
| | (% Dissolution) | |
| EXAMPLE 1 | 100.6% | 88.3% |
| EXAMPLE 2 | 100.1% | 87.4% |
| EXAMPLE 3 | 101.2% | 90.25% |
| Prilosec ® | 98.4% | 81.4% |

The results of Table II demonstrate that the pharmaceutical granules of Examples 1–3 display better release rates (% dissolution) than those of the prior art (Prilosec®) formulation.

EXAMPLE 4

A. Formulation of Pharmaceutical Granules (1) Inert Core: 1294.72 g of sugar, sugar plus starch (in any combinations), or microcrystalline cellulose.
(2) Drug Emulsion:

| | |
|---|---|
| Omeprazole | 168 g |
| Poloxamer 188 | 112 g |
| Purified Water | 720 ml |

(3) Protective Coating:

| | |
|---|---|
| HPMC | 134.4 g |
| PEG 6000 | 13.44 g |
| Purified Water | 1680 ml |

(4) Enteric Coating Layer:

| | |
|---|---|
| Eudragit L30D | 1642.7 g |
| Triethyl Citrate | 24.64 g |
| Purified Water | 400 ml |

B. Method of Preparing the Formulation

The inert core was either bought from companies selling bulk drug material or prepared using the Glatt machine (a fluidized bed particle making machine imported from Germany).

The drug emulsion was prepared by first mixing Poloxamer 188 with purified water to form an emulsified solution, followed by adding omeprazole to the solution while stirring to form the drug emulsion. The emulsion was then placed into the spray gun of the Glatt machine and sprayed onto the core particles while the Glatt machine was set in running (circulating) condition. This would allow the drug to be evenly coated onto the core particles to form drug-coated spherical particles. The drug-coated particles were dried under warm air within the Glatt machine.

Then, a protective coating solution was prepared by first mixing HPMC with purified water to form a solution, followed by adding PEG 6000 to the solution. This coating was then placed into the spray gun of the Glatt machine and sprayed onto the drug-coated particles while the Glatt machine was set in running condition. After the coating was completed, the protective coating-covered particles were again dried under warm air within the Glatt machine.

The enteric coating was prepared according to the same procedures as described in Example 1. This coating was placed into the spray gun of the Glatt machine and sprayed onto the protective coating-covered particles to form the pharmaceutical granules before final drying of the granules to complete the process of making the enteric coating-covered granules.

EXAMPLE 5

A. Formulation of Pharmaceutical Granules (1) Inert Core:

1229.76 g of sugar, sugar plus starch (in any combinations), or microcrystalline cellulose.

(2) Drug Emulsion:

| | |
|---|---|
| Omeprazole | 168 g |
| Poloxamer 188 | 89.6 g |
| Purified Water | 720 ml |

(3) Protective Coating:

| | |
|---|---|
| HPMC | 112 g |
| PEG 6000 | 11.2 g |
| Arginine | 112 g |
| Purified Water | 1723 ml |

(4) Enteric Coating Layer:

| | |
|---|---|
| Eudragit L30D | 1642.7 g |
| Triethyl Citrate | 24.64 g |
| Purified Water | 400 ml |

B. Method of Preparing the Formulation

The method for preparing the formulation as shown in Example 5 was the same as that of Example 4 except that in the protective coating, arginine was added to the solution which contained HMPC, PEG 6000 and purified water.

EXAMPLE 6

A. Formulation of Pharmaceutical Granules (1) Inert Core:

1229.76 g of sugar, sugar plus starch (in any combinations), or microcrystalline cellulose.

(2) Drug Emulsion:

| | |
|---|---|
| Omeprazole | 168 g |
| Poloxamer 188 | 89.6 g |
| Purified Water | 720 ml |

(3) Protective Coating containing two sublayers:

(i) Sublayer 1 (which is next to the drug emulsion layer)

| | |
|---|---|
| HPMC | 44.8 g |
| PEG 6000 | 4.48 g |
| Purified Water | 680 ml |

(ii) Sublayer 2 (which is next to the enteric coating)

| | |
|---|---|
| HPMC | 67.2 g |
| PEG 6000 | 6.72 g |
| Arginine | 112 g |
| Purified Water | 1244 ml |

(4) Enteric Coating Layer:

| | |
|---|---|
| Eudragit L30D | 1642.7 g |
| Triethyl Citrate | 24.64 g |
| Purified Water | 400 ml |

B. Method of Preparing the Formulation

The method for preparing the formulation as shown in Example 6 was the same as that of Example 5 except that there were two sublayers within the protective coating which must be applied sequentially, with sublayer 1 coated directly onto the drug coated particles followed by sublayer 2, which then was coated by the enteric coating to form the pharmaceutical granules.

Tests of the Stability of the Pharmaceutical Formulations as Shown in EXAMPLES 4–6

Table III shows the % dissolution, i.e., the percentage of the drug in Examples 4–6 being released in the solution at pH 1.2 (for 120 minutes) and at pH 6.8 (for 30 minutes). The data from the commercially available omeprazole drug (Prilosec) is included for comparison purpose.

TABLE III

% DISSOLUTION OF THE PHARMACEUTICAL GRANULES OF EXAMPLES 4–6

| | pH 1.2 (120 minutes) | pH 6.8 (30 minutes) |
|---|---|---|
| | (% Dissolution) | |
| EXAMPLE 4 | 92.9% | 87.3% |
| EXAMPLE 5 | 95.4% | 86.0% |
| EXAMPLE 6 | 100.1% | 85.8% |
| Prilosec ® | 98.4% | 81.4% |

The results shown in Table II demonstrate that the pharmaceutical formulations of Examples 4–6 display equal or better release rates (% dissolution) than the prior art (Prilosec®) formulation.

The stability of the pharmaceutical formulations in Examples 4–6 was also tested for decoloration. The test was conducted under the following conditions: temperature was controlled at 45° C., relative humidity was at 75±5%, storage time was for 1 month. The colors of the pharmaceutical granules in Examples 4–6 were white at the time the granules were prepared.

TABLE IV

STABILITY OF THE PHARMACEUTICAL GRANULES AFTER ONE MONTH OF STORAGE AT 45° C. AND 75 ± 5% RELATIVE HUMIDITY

| | COLOR OF THE GRANULES |
|---|---|
| Example 4 | Pale Beige |
| Example 5 | White |
| Example 6 | White |
| Prilosec | Pale Purple |

The results of Table IV indicated that while the % dissolution of the pharmaceutical granules in Example 4 was as good as those in Examples 5–6 and the commercially available omeprazole granules Prilosec®, its stability was probably slightly worse than those of Examples 5–6, although the degree of stability between the granules of Example 4 and Prilosec® was probably comparable. Because the major difference between Example 4 and Examples 5–6 was that the protective coating of Example 4 did not contain arginine, it could therefore conclude that the addition of arginine (or other basic amino acid) in the protective coating had contributed to the stability of the pharmaceutical granules.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. An orally administered pharmaceutical granule comprising:
   an inert core comprising at least one compound and/or mixture selected from the group consisting of starch, a mixture of sugar and starch, and microcrystalline cellulose;
   a drug emulsion deposited on said inert core, wherein said drug emulsion comprises an effective amount of a free base omeprazole or a free base lansoprazole, a non-ionic surfactant, a basic amino acid, and water;
   a protective coating deposited on said drug emulsion, wherein said protective coating comprises at least one film-forming compound which is selected from the group consisting of hydroxypropyl methylcellulose (HPMC), hydroxypropyl cellulose (HPC), polyvinyl pyrrolidone (PVP) and hydroxy methylcellulose (HMC), and a plasticizer; and
   an enteric coating deposited on said protective coating, wherein said enteric coating comprises at least a polymer which is selected from the group consisting of hydroxypropyl methylcellulose phthalate (HPMCP), cellulose acetate phthalate (CAP), and co-polymerized methacrylic acid/methacrylic acid methyl esters, and a plasticizer,
   wherein said plasticizer is one compound selected from the group consisting of triethyl citrate, triacetin, and diethyl phthalate.

2. The orally administered pharmaceutical granule according to claim 1, wherein said drug emulsion contains 30–60 wt % of water, 1–10 wt % of the non-ionic surfactant, and 1–15wt % of the basic amino acid.

3. The orally administered pharmaceutical granule according to claim 1, wherein said basic amino acid is selected from the group consisting of arginine, lysine, histidine, and tryptophane.

4. The orally administered pharmaceutical granule according to claim 1, wherein said non-ionic surfactant is polyoxypropylene-polyoxyethylene copolymers or polysorbates.

5. The orally administered pharmaceutical granule according to claim 1, wherein said polymer and said plasticizer in said enteric layer are at a weight ratio of no less than 10:1.

6. The orally administered pharmaceutical granule according to claim 1, wherein said granule is further encapsulated.

7. The orally administered pharmaceutical granule according to claim 1, wherein said granule is compressed into tablet by mixing with at least an excipient which is selected from the group consisting of lactose, starch, talc, microcrystalline cellulose, and polyethylene glycol (PEG).

8. A process of making an orally administered pharmaceutical granule according to claim 1 comprising:
   obtaining an inert core;
   coating the inert core with a drug emulsion which comprises a free base omeprazole or a free base lansoprazole, a non-ionic surfactant, arginine, and water by spraying said drug emulsion onto said inert core;
   coating the drug emulsion with a protective coating which comprises a film-forming compound, a plasticizer, and water by spraying said protective coating onto said drug emulsion; and
   coating said protective coating with an enteric coating which comprises a polymer, a plasticizer, and water by spraying said enteric coating onto said protective coating,
   wherein said plasticizer is one compound selected from the group consisting of triethyl citrate, triacetin, and diethyl phthalate.

9. A method for treating digestive ulcers and gastritis comprising orally administering to a host in need of such treatment a therapeutically effective amount of a pharmaceutical granule comprising:
   an inert core consisting essentially of at least one compound and/or mixture selected from the group consisting of starch, a mixture of sugar and starch, and microcrystalline cellulose;
   a drug emulsion deposited on said inert core, wherein said drug emulsion comprises an effective amount of a free base omeprazole or a free base lansoprazole, a non-ionic surfactant, a basic amino acid, and water;
   a protective coating deposited on said drug emulsion, wherein said protective coating comprises at least one film-forming compound which is selected from the group consisting of hydroxypropyl methylcellulose (HPMC), hydroxypropyl cellulose (HPC), polyvinyl pyrrolidone (PVP) and hydroxy methylcellulose (HMC), and a plasticizer; and
   an enteric coating deposited on said protective coating, wherein said enteric coating comprises at least a polymer which is selected from the group consisting of hydroxypropyl methylcellulose phthalate (HPMCP), cellulose acetate phthalate (CAP), and co-polymerized methacrylic acid/methacrylic acid methyl esters, and a plasticizer.

10. An orally administered pharmaceutical granule comprising:
- an inert core comprising at least one compound and/or mixture selected from the group consisting of starch, a mixture of sugar and starch, and microcrystalline cellulose;
- a drug emulsion deposited on said inert core, wherein said drug emulsion comprises an effective amount of a free base omeprazole or a free base lansoprazole, a non-ionic surfactant, and water, wherein said drug emulsion does not contain an alkaline salt or compound;
- a protective coating deposited on said drug emulsion, wherein said protective coating comprises at least one film-forming compound which is selected from the group consisting of hydroxypropyl methylcellulose (HPMC), hydroxypropyl cellulose (HPC), polyvinyl pyrrolidone (PVP) and hydroxy methylcellulose (HMC), and optionally an excipient; and
- an enteric coating deposited on said protective coating, wherein said enteric coating comprises at least a polymer which is selected from the group consisting of hydroxypropyl methylcellulose phthalate (HPMCP), cellulose acetate phthalate (CAP), and co-polymerized methacrylic acid/methacrylic acid methyl esters, and a plasticizer,
- wherein said plasticizer is one compound selected from the group consisting of triethyl citrate, triacetin, and diethyl phthalate.

11. The orally administered pharmaceutical granule according to claim 10, wherein said non-ionic surfactant is polyoxypropylene-polyoxyethylene copolymers or polysorbates.

12. The orally administered pharmaceutical granule according to claim 10, wherein said excipient is polyethylene glycol 6000 having a molecular weight between 7000 and 9000.

13. The orally administered pharmaceutical granule according to claim 10, wherein said polymer and said plasticizer in said enteric layer are at a weight ratio of no less than 10:1.

14. The orally administered pharmaceutical granule according to claim 10, wherein said protective coating further comprises a basic amino acid selected from the group consisting of arginine, lysine, histidine, and tryptophan.

15. The orally administered pharmaceutical granule according to claim 11, wherein said protective coating comprises one or more sublayers.

16. The orally administered pharmaceutical granule according to claim 15, wherein at least one of the sublayers contains a basic amino acid selected from the group consisting of arginine, lysine, histidine, and tryptophan.

17. The orally administered pharmaceutical granule according to claim 15, wherein none of the sublayers of the protective coating contains an alkaline salt or compound.

18. The orally administered pharmaceutical granule according to claim 10, wherein said granule is further encapsulated.

19. The orally administered pharmaceutical granule according to claim 10, wherein said granule is compressed into tablet by mixing with at least one said excipient which is selected from the group consisting of lactose, starch, talc, microcrystalline cellulose, and polyethylene glycol (PEG).

20. A process of making an orally administered pharmaceutical granule according to claim 10 comprising:
- obtaining an inert core;
- coating the inert core with a drug emulsion which comprises a free base omeprazole or a free base lansoprazole, a non-ionic surfactant, arginine, and water by spraying said drug emulsion onto said inert core;
- coating the drug emulsion with a protective coating which comprises a film-forming compound, a plasticizer, and water by spraying said protective coating onto said drug emulsion; and
- coating said protective coating with an enteric coating which comprises a polymer, a plasticizer, and water by spraying said enteric coating onto said protective coating,
- wherein said plasticizer is one compound selected from the group consisting of triethyl citrate, triacetin, and diethyl phthalate.

21. A method for treating digestive ulcers and gastritis comprising orally administering to a host in need of such treatment a therapeutically effective amount of a pharmaceutical granule comprising:
- an inert core consisting essentially of at least one compound and/or mixture selected from the group consisting of starch, a mixture of sugar and starch, and microcrystalline cellulose;
- a drug emulsion deposited on said inert core, wherein said drug emulsion comprises an effective amount of a free base omeprazole or a free base lansoprazole, a non-ionic surfactant, and water, wherein said drug emulsion does not contain an alkaline salt or compound;
- a protective coating deposited on said drug emulsion, wherein said protective coating comprises at least one film-forming compound which is selected from the group consisting of hydroxypropyl methylcellulose (HPMC), hydroxypropyl cellulose (HPC), polyvinyl pyrrolidone (PVP) and hydroxy methylcellulose (HMC), and optionally an excipient; and
- an enteric coating deposited on said protective coating, wherein said enteric coating comprises at least a polymer which is selected from the group consisting of hydroxylpropyl methylcellulose phthalate (HPMCP), cellulose acetate phthalate (CAP), and co-polymerized methacrylic acid/methacrylic acid methyl esters, and a plasticizer.

22. An orally administered pharmaceutical granule comprising:
- an inert core selected from the groups of compounds and/or mixtures consisting essentially of starch, a mixture of sugar and starch, and microcrystalline cellulose and mixtures thereof;
- a drug emulsion deposited on said inert core, wherein said drug emulsion comprises an effective amount of a freebase omeprazole or a free base lansoprazole, a non-ionic surfactant, and water, wherein said drug emulsion does not contain an alkaline salt or compound;
- a first protective coating deposited on said drug emulsion, wherein said first protective coating does not contain an alkaline salt or compound and wherein said first protective coating comprises at least one film-forming compound which is selected from the group consisting of hydroxypropyl methylcellulose (HPMC), hydroxypropyl cellulose (HPC), polyvinyl pyrrolidone (PVP) and hydroxy methylcellulose, and optionally an excipient;

a second protective coating deposited on said first protective coating, wherein said second protective coating comprises at least one film-forming compound which is selected from the group consisting of hydroxypropyl methylcellulose (HPMC), hydroxypropyl cellulose (HPC), polyvinyl pyrrolidone (PVP) and hydroxy methylcellulose, and optionally an excipient;

an enteric coating deposited on said second protective coating, wherein said enteric coating comprises at least a polymer which is selected from the group consisting of methylcellulose phthalate (HPMCP), cellulose acetate phthalate (CAP), and co-polymerized methacrylic acid/methacrylic acid methyl esters, and a plasticizer.

23. The orally administered pharmaceutical granule according to claim 22, wherein said second protective coating further comprises a basic amino acid which is selected from the group consisting of arginine, lysine, histidine, and tryptophan.

* * * * *